United States Patent [19]

Nagasawa et al.

[11] Patent Number: 4,973,739

[45] Date of Patent: Nov. 27, 1990

[54] PROCESS FOR PRODUCTION OF CARBOXYLIC ACID ESTERS

[75] Inventors: Seiji Nagasawa; Hideo Ikarashi; Yoshio Kawai; Hiroyuki Hirayama, all of Niigata, Japan

[73] Assignee: Mitsubishi Gas Chemical Company, Inc., Tokyo, Japan

[21] Appl. No.: 336,729

[22] Filed: Apr. 12, 1989

[30] Foreign Application Priority Data

May 16, 1988 [JP] Japan .................................. 63-116971

[51] Int. Cl.$^5$ .............................................. C07C 69/76
[52] U.S. Cl. ...................................... 560/103; 560/38; 560/60; 560/106; 560/155; 560/173; 560/179; 560/188; 560/205; 560/215; 560/265; 564/137
[58] Field of Search .................. 560/38, 60, 103, 155, 560/179, 215, 106, 173, 188, 205, 265

[56] References Cited

U.S. PATENT DOCUMENTS

| 4,055,590 | 10/1977 | Gruber et al. | 560/179 |
|---|---|---|---|
| 4,161,609 | 7/1979 | Cramer | 560/215 |
| 4,613,684 | 9/1986 | Aoyama et al. | 560/179 |

FOREIGN PATENT DOCUMENTS

| B12528524 | 11/1976 | Fed. Rep. of Germany . |
|---|---|---|
| 3436608A1 | 5/1985 | Fed. Rep. of Germany . |
| 53-141216 | 12/1978 | Japan . |
| 53-144524 | 12/1978 | Japan . |
| 57-67534 | 4/1982 | Japan . |
| 58-49338 | 3/1983 | Japan . |
| 58-55444 | 4/1983 | Japan . |
| 60-78937 | 5/1985 | Japan . |

OTHER PUBLICATIONS

Patent Abstracts of Japan for: (1) 53-141216, (2) 53-144524, (3) 57-67534, (4) 58-49338, (5) 58-55444 and (6) 60-78937.
Patents Abstracts of Japan, unexamined applications, section C, vol. 7, No. 139, Jun. 17, 1983, The Patent Office Japanese Gov. p. 28 C 172 *Kokai-No. 58-55444 (Mitsubishi)*.

*Primary Examiner*—Michael L. Shippen
*Attorney, Agent, or Firm*—Frishauf, Holtz, Goodman & Woodward

[57] ABSTRACT

Carboxylic acid esters, industrially important compounds, are efficiently obtained by reacting carboxylic acid amides with formic acid esters in the presence of an inorganic solid acid catalyst.

7 Claims, No Drawings

PROCESS FOR PRODUCTION OF CARBOXYLIC ACID ESTERS

BACKGROUND OF THE INVENTION

1. Field of the Invention

The present invention relates to a process for efficient production of carboxylic acid esters, from carboxylic acid amides and formic acid esters.

2. Description of Related Arts

Carboxylic acid esters are industrially important compounds. These carboxylic acid esters can be produced from carboxylic acid amides: for example, methyl acetate is produced from acetic acid amides; methyl methacrylate from methacrylic acid amide; methyl acrylate from acrylic acid amide; or methyl α-hydroxyisobutyrate from α-hydroxyisobutyric acid amide. For producing carboxylic acid esters from carboxylic acid amides, a method of reacting carboxylic acid amides with alcohols in the presence of sulfuric acid is well known. This method is widely employed for industrial production of methyl methacrylate. This method, however, has disadvantages in that a large amount of acidic ammonium sulfate results as a by-product, leading to a marked increase in production costs owing to its disposal, and an expensive corrosion-resistant apparatus is also required.

In order to overcome the above problems, a method of producing carboxylic acid esters by reacting carboxylic acid amides and alcohols without the use of sulfuric acid has been proposed. In Japanese Patent Application Laid-Open Nos. 3015/1977, 141216/1978 and 144524/1978, for example, the reaction is carried out in a liquid phase in the presence of e.g. metal salts or metal alcoholates. On the other hand, in Japanese Patent Application Laid-Open Nos. 67534/1982 and 49338/1983, the reaction is carried out in a gas phase in the presence of a solid acid catalyst.

These methods, however, have disadvantages in that the yield of the desired carboxylic acid ester or its selectivity is low and thus are not satisfactory in commercial practice thereof. Moreover, in commercial practice, they suffer from problems in that: (1) the reaction should be carried out at high temperatures, (2) in case of the liquid phase reaction, high pressure is needed, (3) a large amount of ammonia is produced during the reaction and thus its recovery and separation is needed, and (4) the reaction of the ammonia with carboxylic acids as by-product leads to the formation of ammonium salts thereof.

A method of producing carboxylic acid esters and formamide by reacting carboxylic acid amides with formic acid esters has been developed, as described in Japanese Patent Application Laid-Open Nos. 55444/1983 and 78937/1985.

In Japanese Patent Application Laid-Open No. 55444/1983, a main catalysts comprising metal salts of organic or inorganic acids, or metal chelate compounds, and an accelerator comprising nitrogen or phosphorus-containing organic compounds are used in combination. In one of the examples, the reaction was carried out at 185 to 250° C for 2 to 4.5 hours, and the desired carboxylic acid ester was obtained in a yield of 16.3 to 78.9%. This yield, however, cannot be said to be sufficiently high, and moreover the catalyst system is expensive.

In Japanese Patent Application Laid-Open No. 78937/1985, a catalyst system consisting of a combination of amidine or tertiary amine and metal carbonyl is used, and the reaction is carried out under pressure of carbon monoxide. However, although the selectivity of the carboxylic acid ester is relatively high, this method has disadvantages in that high pressure is needed for the reaction, highly toxic metal carbonyl is used, and the catalyst system is expensive.

SUMMARY OF THE INVENTION

An object of the present invention is to provide an improved process for producing carboxylic acid esters from carboxylic acid amides and formic acid esters.

Another object of the present invention is to provide improved process for producing both carboxylic acid esters and formamide from starting materials as described above.

It has been found that a solid acid catalyst, e.g. silica, alumina, silica-alumina or zeolite is effective for producing carboxylic acid esters, and that if such a solid acid catalyst is used, it is not necessary to maintain the reaction system under the pressure of carbon monoxide. In the case of a solid acid catalyst, recovery of the catalyst and its reuse are very easy and, therefore, the process of the present invention is extremely significant for industrial use.

The present invention relates to a process for production of carboxylic acid ester which comprises reacting carboxylic acid amide and formic acid ester in the presence of an inorganic solid acid catalyst.

DESCRIPTION OF PREFERRED EMBODIMENTS

Carboxylic acid amides to be used in the present invention include aliphatic or aromatic carboxylic acid amides, and α-hydroxy or α-aminocarboxylic acid amides. These amides can be prepared by hydrolyzing nitriles, or by reacting amines and carbon monoxide. Specific examples are acetamide, lactic acid amide, acrylic acid amide, methacrylic acid amide, α-hydroxyisobutyric acid amide, benzamide, valine amide and alanineamide.

Formic acid esters to be used in the present invention are those prepared from formic acid, and aliphatic alcohols having 1 to 10 carbon atoms or alicyclic alcohols having 4 to 10 carbon atoms. Specific examples of aliphatic alcohols are methanol, ethanol, propanol, butanol and octanol. Specific examples of the alicyclic alcohols are cyclohexanol and cycloheptanol.

The catalyst to be used in the present invention is a catalyst generally called a "solid acid catalyst". Typical examples are silica, alumina, silica-alumina, titania, zirconia, solid phosphoric acid, zeolites, composite compounds of the above compounds, and composite compounds comprising the above compounds and a carrier. This catalyst can be used in the state of suspension or flow in the reaction system as a powder. It can be also used in a suitable size of molding made of the above compound as a fixed bed catalyst.

The reaction of the present invention is an equilibrium reaction, and the conversion greatly varies according to the molar ratio of formic acid ester to carboxylic acid amide. From an industrial production viewpoint of carboxylic acid ester, the amount of the formic acid ester is preferably 1 to 10 moles per mole of carboxylic acid amide.

Carboxylic acid amides are generally in solid state at room temperature. Since the solubility of carboxylic acid amide in formic acid ester is low in many cases, it is desirable to use a suitable solvent in the present invention. An alcohol constituting the formic acid ester is preferably used for the solvent.

The reaction temperature and period of time can be chosen from a wide range depending on the kind of the starting material, the amount of the catalyst charged, and the conversion objective. In general, the reaction temperature is preferably 170 to 250° C and more preferably 190 to 230° C, and the reaction period of time is preferably 0.1 to 5 hours and more preferably 0.2 to 3 hours.

The present invention is described in greater detail with reference to the following examples, although it is not intended to be limited thereto.

EXAMPLE 1

6.2 g (0.06 mole) of α-hydroxyisobutyric acid amide, 18 g (0.3 mole) of methyl formate, 9.6 g (0.3 mole) of methanol, and 2 g of a silica-alumina catalyst (N631H produced by Nikki Chemical Co., Ltd.) powder which had been calcined at 800° C. for 3 hours were placed in a 100-milliliter stainless steel autoclave, and the mixture thus obtained was reacted at 200° C. for 3 hours.

After completion of the reaction, the reaction mixture was cooled to room temperature and then the catalyst was removed by filtration. The product was subjected to a gas chromatographic analysis. This analysis showed that the conversion of α-hydroxyisobutyric acid amide was 56.5%, the selectivity into methyl α-hydroxyisobutyrate was 94.1%, and the selectivity into formamide (based on the reacted α-hydroxyisobutyric acid amide) was 88.5%.

EXAMPLE 2

The procedure of Example 1 was repeated with the exception that 3.5 g (0.06 mole) of acetic acid amide was used as the carboxylic acid amide.

The conversion of acetic acid amide was 60.5%, the selectivity into methyl acetate was 96.5% and the selectivity into formamide (based on the reacted acetic acid amide) was 90.9%.

EXAMPLE 3

The procedure of Example 1 was repeated with the exception that 7.3 g (0.06 mole) of benzamide was used as the carboxylic acid amide.

The conversion of benzamide was 55.1%, the selectivity into methyl benzoate was 95.1% and the selectivity into formamide was 87.6%.

EXAMPLE 4

The procedure of Example 1 was repeated with the exception that an alumina catalyst (N612 produced by Nikki Chemical Co., Ltd.) was used as the catalyst, and that the reaction temperature and time period of time were changed to 220° C and 1 hour, respectively.

The conversion of α-hydroxyisobutyric acid amide was 59.4%, the selectivity into methyl α-hydroxyisobutyrate was 92.8% and the selectivity into formamide was 85.2%.

EXAMPLE 5

The procedure of Example 1 was repeated with the exception that 30.6 g (0.3 mole) of butyl formate was used as the formic acid ester and that 22.2 g (0.3 mole) of butanol was used as the alcohol.

The conversion of α-hydroxyisobutyric acid amide was 54.3%, the selectivity into butyl α-hydroxyisobutyrate was 90.9% and the selectivity into formamide was 86.5%.

COMPARATIVE EXAMPLE 1

The procedure of Example 1 was repeated with the exception that the catalyst was not used.

The conversion of α-hydroxyisobutyric acid amide was 24.8%, the selectivity into methyl α-hydroxyisobutyrate was 87.6% and the selectivity into formamide was 84.7%.

What is claimed is:

1. In a process for production of carboxylic acid ester which comprises reacting carboxylic acid amide and formic acid ester in the presence of a catalyst the improvement wherein the catalyst is an inorganic solid acid catalyst which is at least one member selected from the group consisting of alumina, silica-alumina, titania, zirconia, solid phosphoric acid, zeolite, composite compounds of the above compounds and composite compounds composed of the above compounds and a carrier.

2. The process as claimed in claim 1, wherein the carboxylic acid amide is aliphatic carboxylic acid amide, aromatic carboxylic acid amide, aliphatic α-hydroxyl carboxylic acid amide, aromatic α-hydroxyl carboxylic acid amide, aliphatic α-aminocarboxylic acid amide or aromatic α-aminocarboxylic acid amide.

3. The process as claimed in claim 1, wherein the carboxylic acid amide is at least one compound selected from the group consisting of acetamide, lactic acid amide, acrylic acid amide, methacrylic acid amide, α-hydroxyisobutyric acid amide, benzamide, valine amide and alanineamide.

4. The process as claimed in claim 1, wherein the formic acid ester is at least one compound prepared by reacting formic acid with aliphatic alcohols having 1 to 10 carbon atoms or alicyclic alcohols having 4 to 10 carbon atoms.

5. The process as claimed in claim 1, wherein the amount of the formic acid ester is 1 to 10moles per mole of the carboxylic acid amide.

6. The process as claimed in claim 2, wherein the carboxylic acid amide is at leas tone compound selected from the group consisting of acetamide, lactic acid amide, acrylic acid amide, methacrylic acid amide, α-hydroxyisobutyric acid amide, benzamide, valine amide and alanineamide and the formic acid ester is at least one compound prepared by reacting formic acid with aliphatic alcohols having 1 to 10 carbon atoms or alicyclic alcohols having 4 to 10 carbon atoms.

7. The process as claimed in claim 6, wherein the amount of the formic acid ester is 1 to 10 moles per mole of the carboxylic acid amide.

* * * * *